(12) United States Patent
Mizutani

(10) Patent No.: US 7,666,605 B2
(45) Date of Patent: Feb. 23, 2010

US007666605B2

(54) METHOD FOR PROGNOSTIC EVALUATION OF CARCINOMA USING ANTI-P-LAP ANTIBODY

(75) Inventor: Shigehiko Mizutani, Mie (JP)

(73) Assignee: Suntory Holdings Limited, Osaka (JP)

( * ) Notice: Subject to any disclaimer, the term of this patent is extended or adjusted under 35 U.S.C. 154(b) by 0 days.

(21) Appl. No.: 10/575,763

(22) PCT Filed: Sep. 15, 2004

(86) PCT No.: PCT/JP2004/013883

§ 371 (c)(1),
(2), (4) Date: Apr. 13, 2006

(87) PCT Pub. No.: WO2005/038462

PCT Pub. Date: Apr. 28, 2005

(65) Prior Publication Data

US 2007/0020705 A1 Jan. 25, 2007

(30) Foreign Application Priority Data

Oct. 21, 2003 (JP) ............................ 2003-360638

(51) Int. Cl.
*G01N 33/53* (2006.01)
*C07K 16/00* (2006.01)
*A61K 39/395* (2006.01)

(52) U.S. Cl. .................. 435/7.1; 530/387.1; 530/389.1; 530/389.7; 424/130.1; 424/138.1; 424/174.1

(58) Field of Classification Search ........................ None
See application file for complete search history.

(56) References Cited

OTHER PUBLICATIONS

Suzuki, Y., Shibata, K., Kikkawa, F., Kajiyama, H., Ino, K., Nomura, S., Tsujimoto, M., and Mizutani, S. Possible role of placental leucine aminopeptidase in the antiproliferative effect of oxytocin in human endometrial adenocarcinoma. 2003. Clinical Cancer Research, vol. 9, pp. 1528-1534.*
Stinghen, S.T., Moura, J.F., Zancanella, P., Rodrigues, G.A., Pianovski, M.A., Lalli, E., Arnold, D.L., Minozzo, J.C., Callefe, L.G., Riberio, R.C., and Figueiredo, B.C. Specific immunoassays for placental alkaline phosphatase as a tumor marker. Journal of Biomedicine and Biotechnology, 2006. pp. 1-8.*
Suzuki Yuka et al. "Possible Role of Placental Leucine Aminopeptidase In The Antiproliferative Effect of Oxytocin In Human Endometrial Adenocarcinoma." *Clinical Cancer Research: An Official Journal of the American Association for Cancer Research*. vol. 9, No. 4, Apr. 2003.
Toda Shigeru et al. "Existence of Placental Leucine Aminopeptidase/Oxytocinase/Insulin-regulated Membrane Aminopeptidase In Human Endometrial Epithelial Cells." *The Journal of Clinical Endocrinology and Metabolism*. vol. 87, No. 3, Mar. 2002.
Toda Shigeru et al., "Existence of placental leucine aminopeptidase/oxytocinase/insulin-regulated membrane aminopeptidase in human endometrial cells" The Journal of Clinical Endocrinology and Metabolism, vol. 87, No. 3, Mar. 2002, pp. 1384-1389 (Japanese language only).
International Preliminary Report on Patentability dated Apr. 24, 2006, for International PCT Application No. PCT/JP2004/013883.
Lotocki et al., "Stage I endometrial adenocarcinoma: Treatment results in 835 patents," *American Journal of Obstetrics and Gynecology*, vol. 146, No. 2, May 15, 1983, pp. 141-145.
Morrow et al., "Relationship between Surgical-Pathological Risk Factors and Outcome in Clinical Stage I and II Carcinoma of the Endometrium: A gynecologic Oncology Group Study,"*Gynecologic Oncology*, vol. 40, 1991, pp. 55-65.
Tsujimoto et al., "Identification of Human Placental Leucine Aminopeptidase as Oxytocinase," *Archives of Biochemistry and Biophysics*, vol. 292, No. 2, Feb. 1, 1992, pp. 388-392.
Keller et al., "Cloning and Characterization of a Novel Insulin-regulated Membrane Aminopeptidase from Glut4 Vesicles," *Journal of Biological Chemistry*, vol. 270, No. 40, Oct. 6, 1995, pp. 23612-23618.
Shibata et al., "OS35-3 Placental Leucine Aminopeptidase (P-LAP) Can be a Prognostic Factor for Endometrial Endometrioid Adenocarcinoma," *J. of Japan Soc. of Clin. Oncol.*, vol. 38, No. 2 (Sep. 16, 2003) (Japanese and English Language translation).

* cited by examiner

*Primary Examiner*—David J. Blanchard
*Assistant Examiner*—Anne M. Gussow
(74) *Attorney, Agent, or Firm*—Drinker Biddle & Reath LLP

(57) ABSTRACT

The present invention provides a reagent for prognostic evaluation of carcinoma patients, comprising an anti-P-LAP antibody as an active ingredient. Also, the present invention provides a method for determination of P-LAP which is a prognostic factor in carcinoma patients comprising (a) a step of contacting carcinoma tissues obtained from carcinoma patients by surgical operation with an anti-P-LAP antibody and (b) a step of measuring the intensity of the specific antigen-antibody reaction between P-LAP present in the carcinoma tissues and anti-P-LAP antibody.

3 Claims, 4 Drawing Sheets

METHOD FOR PROGNOSTIC EVALUATION OF CARCINOMA USING ANTI-P-LAP ANTIBODY

RELATED APPLICATION DATA

This application is a §371 National Stage Application of PCT International Application No. PCT/JP2004/013883 filed Sep. 15, 2004, which claims priority to Japanese Application No. 2003-360638, filed in Japan on Oct. 21, 2003.

TECHNICAL FIELD

The present invention relates to a reagent for diagnosis and/or prognostic evaluation of carcinoma, comprising determination of placental leucine aminopeptidase (P-LAP) which is a diagnostic and/or prognostic factor in carcinoma, a method for determination of P-LAP in carcinoma tissues, and a method for prognostic evaluation of carcinoma.

BACKGROUND ART

The number of carcinoma patient has been increasing these days. For example, endometrial endometrioid adenocarcinoma, including endometrial carcinoma and endometrioid adenocarcinoma, is a common gynecological malignancy in the United States. Recently, the incidence of this disease is increasing in Japan. Also, it is known that a significant number of patients with early-stage endometrial endometrioid adenocarcinoma develop both localized recurrence and distant metastasis (Non-patent literature 1).

Meanwhile, for carcinoma patients who have undergone surgical operation, accurate prognostic evaluation in early stage is extremely important for proper post-operative treatment. For example, a chemotherapy having a risk of side effect should be avoided for patients with good prognosis who do not need chemotherapy. On the other hand, appropriate treatment including chemotherapy should be provided to patients who are at high risk of recurrence of carcinoma or reoperation in order to prevent recurrence of carcinoma or to avoid reoperation. Hence, various researches have been conducted to find prognostic factors, however, a credible prognostic factor has not yet being discovered.

With regard to endometrial adenocarcinoma, for example, several clinicopathological indicators are currently used for prognosis, such as the surgical stage of disease, lymph node involvement, myometrial infiltration, histological cell types, differentiation grade of carcinoma, intraperitoneal spread, cervical extension, vascular invasion and the like (non-patent literature 2). However, it cannot be said that the clinicopathological indicators described in the literature are completely reliable indicators for prognosis of endometrial endometrioid adenocarcinoma.

On the other hand, P-LAP is a cell surface aminopeptidase, and is a synonym for oxytocinase (non-patent literature 3). P-LAP is also referred to as insulin-regulated membrane aminopeptidase associated with the glucose transporter 4 (GLUT4) containing vesicles (non-patent literature 4). Recently, it was shown that P-LAP is present in both human endometrial endometrioid adenocarcinoma tissues and cells, and that it works as a regulator of carcinoma cell growth (non-patent literature 5). Also, there has been reported the intriguing changes of P-LAP in normal endometrium during menstrual cycle (non-patent literature 6). However, it has not been known that P-LAP can be a prognostic factor in carcinoma.

(Non-patent literature 1) Am. J. Obstet. Gynecol., 1983; 146: 141-144
(Non-patent literature 2) Gynecol. Oncol., 1991; 40: 55-65
(Non-patent literature 3) Arch. Biochem. Biophys., 1992; 292: 388-392
(Non-patent literature 4) J. Biol. Chem., 1995; 270: 23612-23618
(Non-patent literature 5) Clin. Cancer Res., 2003; 9(4): 1528-1534
(Non-patent literature 6) J. Clin. Endocrinol. Metab., 2002; 87: 1384-1389

DISCLOSURE OF THE INVENTION

An object of the present invention is to provide a reagent for diagnosis and/or prognostic evaluation of carcinoma. Another object of the present invention is to provide a method for determination of prognostic factors in carcinoma. A still another object of the present invention is to provide a method for prognostic evaluation of carcinoma.

The present inventors conducted various studies to solve the aforementioned problems. As a result, they found that P-LAP could be a prognostic factor in carcinoma, including gynecological carcinoma such as endometrial endometrioid adenocarcinoma, cervical carcinoma, ovarian caricnoma, etc., and thus completed the present invention.

Namely, the present invention relates to (1) A reagent for diagnosis and/or prognostic evaluation of carcinoma, which comprises an anti-P-LAP antibody as an active ingredient;

(2) The reagent according to the above (1), wherein the carcinoma is gynecological carcinoma;

(3) The reagent according to the above (2), wherein the gynecological carcinoma is endometrial endometrioid adenocarcinoma, cervical carcinoma or ovarian carcinoma;

(4) The reagent according to any one of the above (1) to (3), wherein the anti-P-LAP antibody is an anti-human P-LAP antibody;

(5) The reagent according to any one of the above (1) to (3), wherein the anti-P-LAP antibody is an anti-human P-LAP polyclonal antibody;

(6) A method for determination of P-LAP which is a prognostic factor in carcinoma, which comprises (a) a step of contacting carcinoma tissues obtained from carcinoma patients with an anti-P-LAP antibody, and (b) a step of measuring the intensity of the specific antigen-antibody reaction between P-LAP present in the carcinoma tissues and anti-P-LAP antibody;

(7) The method according to the above (6), wherein the carcinoma is gynecological carcinoma;

(8) The method according to the above (7), wherein the gynecological carcinoma is endometrial endometrioid adenocarcinoma, cervical carcinoma or ovarian carcinoma;

(9) The method according to any one of the above (6) to (8), wherein the anti-P-LAP antibody is an anti-human P-LAP antibody;

(10) The method according to any one of the above (6) to (8), wherein the anti-P-LAP antibody is an anti-human P-LAP polyclonal antibody;

(11) A method for prognostic evaluation of carcinoma, which comprises (a) a step of contacting carcinoma tissues obtained from carcinoma patients with an anti-P-LAP antibody, (b) a step of measuring the intensity of the specific antigen-antibody reaction between P-LAP present in the carcinoma tissues and anti-P-LAP antibody, and (c) a step of correlating the intensity of the specific antigen-antibody reaction with prognosis of carcinoma;

(12) The method according to the above (11), wherein the carcinoma is gynecological carcinoma;

(13) The method according to the above (12), wherein the gynecological carcinoma is endometrial endometrioid adenocarcinoma, cervical carcinoma or ovarian carcinoma;

(14) The method according to any one of the above (11) to (13), wherein the anti-P-LAP antibody is an anti-human P-LAP antibody;

(15) The method according to any one of the above (11) to (13), wherein the anti-P-LAP antibody is an anti-human P-LAP polyclonal antibody; and

(16) An immunoassay kit for determination of the amount of P-LAP present in carcinoma tissues obtained from carcinoma patients, which comprises an anti-P-LAP antibody and a marker enzyme for determination of the amount of the P-LAP bound to the anti-P-LAP antibody.

An accurate prognostic evaluation of carcinoma can be achieved when the reagent of the present invention is used and the amount of P-LAP present in carcinoma tissues obtained from patients with carcinoma, including gynecological carcinoma such as endometrial endometrioid adenocarcinoma, is determined. This makes it possible to provide postoperative patients with appropriate treatment.

Figure 1:
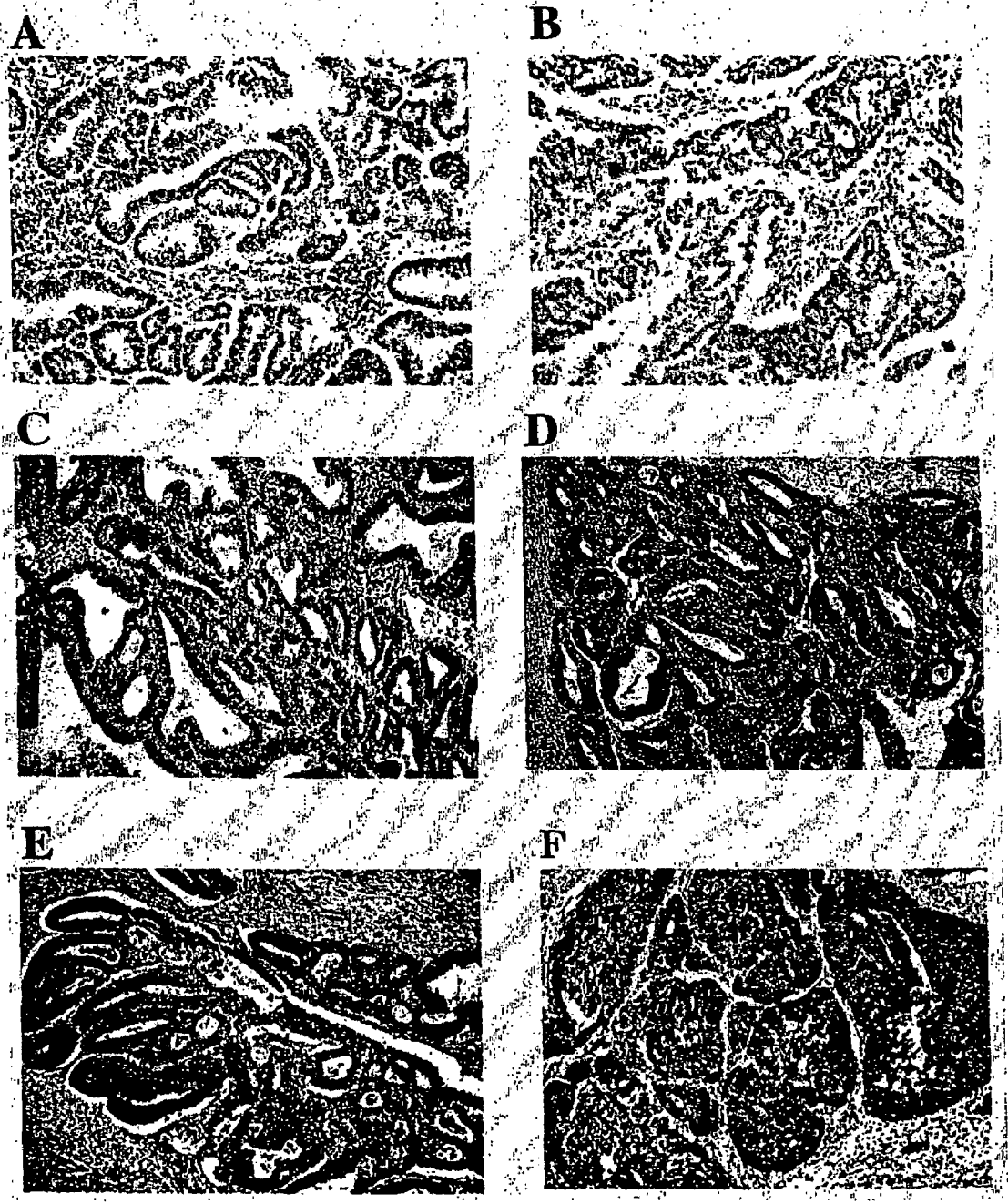
FIG. 1 shows preferential overexpression of P-LAP in human endometrioid adenocarcinoma tissues.

In the FIG. 1, symbol A shows negative P-LAP immunoreactivity in grade 1 endometrioid adenocarcinoma tissues;

symbol B shows negative P-LAP immunoreactivity in grade 2 endometrioid adenocarcinoma tissues;

symbol C shows weakly positive P-LAP immunoreactivity in grade 1 endometrioid adenocarcinoma tissues;

symbol D shows strongly positive P-LAP immunoreactivity in grade 1 endometrioid adenocarcinoma tissues;

symbol E shows strongly positive P-LAP immunoreactivity in grade 2 endometrioid adenocarcinoma tissues; and symbol F shows strongly positive P-LAP immunoreactivity in grade 3 endometrioid adenocarcinoma tissues.

BEST MODE FOR CARRYING OUT THE INVENTION

Anti-P-LAP antibody which is an active ingredient of the reagent of the present invention is preferably an anti-human P-LAP antibody. Also, the anti-human P-LAP antibody may be a polyclonal antibody or a monoclonal antibody. Those antibodies can be produced using P-LAP as antigen according to conventional methods. For example, it is possible to produce an anti-human P-LAP polyclonal antibody by the method described in PLACENTA, Nakanishi et al., 2000, vol. 21, p.628-634.

Carcinoma tissues obtained from carcinoma patients are used for prognostic evaluation of carcinoma using the reagent of the present invention. Although there is no limitation on the types of carcinoma, examples of carcinoma preferably include gynecological carcinoma such as endometrial endometrioid adenocarcinoma (including endometrial carcinoma and endometrioid adenocarcinoma), ovarian carcinoma, cervical carcinoma, etc.; pancreatic carcinoma; prostate carcinoma and the like, more preferably gynecological carcinoma such as endometrial endometrioid adenocarcinoma, cervical carcinoma, ovarian carcinoma, etc.

The carcinoma tissues obtained from carcinoma patients are fixed in formalin, embedded in paraffin and made into sections of appropriate size to prepare carcinoma tissue samples, and then the amount of P-LAP in carcinoma tissues is determined using those samples.

The amount of P-LAP present in the tissues of carcinoma patients can be determined by immunoassay, or more specifically, by (a) contacting carcinoma tissues obtained from carcinoma patients with an anti-P-LAP antibody, followed by (b) measuring the intensity of the specific antigen-antibody reaction between P-LAP present in the carcinoma tissues and anti-P-LAP antibody.

When the streptavidin-biotin-peroxidase method, for example, is employed for the aforementioned immunoassay, the method may be carried out as follows.

Firstly, deparaffinized carcinoma tissue samples are incubated with hydrogen peroxide to block endogenous peroxidase, and then further incubated with normal goat serum to block non-specific binding. An anti-P-LAP antibody (primary antibody) is added thereto to effect antigen-antibody reaction, followed by addition of horseradish peroxidase-conjugated streptavidin for binding reaction. Conditions for the antigen-antibody reaction and the binding reaction are not specifically limited, and may be similar to those usually employed for those types of reactions.

A chromogenic substrate such as 3-amino-9-ethylcarbazole is acted on the complex obtained as above (complex of P-LAP, anti-P-LAP antibody, biotinylated goat anti-rabbit IgG and peroxidase-conjugated streptavidin) in the presence of hydrogen peroxide to develop color, and counterstained with hematoxylin. The amount of P-LAP in the carcinoma tissues can be determined by analysis of the staining intensity of samples.

Enzymes other than peroxidase can be used as a marker for determination of the amount of P-LAP in carcinoma tissues as long as anti-P-LAP antibody bound to P-LAP can be detected by the method. Examples of such enzyme include malic dehydrogenase, staphylococcal nuclease, delta-5-steroid isomerase, yeast alcohol dehydrogenase, alpha-glycerol phosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase, acetylcholineesterase and the like.

An assay kit can be provided by combining the aforementioned marker enzyme with an anti-P-LAP antibody. The kit optionally comprises a reagent for binding an anti-P-LAP antibody with a marker enzyme, a reaction solution, a substrate, a substrate diluent and/or a reaction stop solution.

The marker may be a radioactive isotope, a fluorescent material, a chemiluminescent material, a bioluminescent material, etc. other than enzyme. These markers are attached to desired molecules by a common technique conventionally used by those skilled in the art.

Next, the intensity of P-LAP immunoreactivity (intensity of the specific antigen-antibody reaction between P-LAP and anti-P-LAP antibody) in carcinoma tissues measured above is correlated with prognosis of carcinoma, thereby prognosis of the carcinoma can be evaluated. The aforementioned process is explained below by using the case of endometrial endometrioid adenocarcinoma, including endometrioid adenocarcinoma, as an example.

The intensity of the specific antigen-antibody reaction between P-LAP and anti-P-LAP antibody, for example P-LAP immunostaining intensity, determined by the above immunoassay was scored on a three-tiered scale of negative (−), weakly positive (+) and strongly positive (++), and the correlation between the intensity and disease-free interval in endometrial endometrioid adenocarcinoma, including endometrioid adenocarcinoma, cases was examined. The results revealed that the disease-free survival rate for patients who had negative or weakly positive intensity was significantly higher than that for patients who had strongly positive intensity. In addition, further studies showed that any of the characteristics including surgical stage of the disease, tumor grade (differentiation stage), myometrial invasion, vascular infiltration and lymph node involvement, had a positive correlation with P-LAP immunostaining intensity.

Those facts indicate that P-LAP present in carcinoma tissues is a reliable prognostic marker for carcinoma. Therefore, prognostic evaluation of carcinoma can be achieved when the amount of P-LAP present in carcinoma tissues obtained from carcinoma patients is determined by the aforementioned immunoassay using an anti-P-LAP antibody, and then the intensity of immunoreaction between P-LAP and anti-P-LAP antibody is correlated with prognosis of carcinoma.

EXAMPLES

The present invention will be further illustrated by way of the following Examples, although they do not limit the present invention.

Example 1

(1) Patients

Ninety-nine patients with endometrial endometrioid adenocarcinoma, including endometrial carcinoma and endometrioid adenocarcinoma, who had been surgically treated at Nagoya University Hospital between January 1993 and December 2000 were included in this study. Diagnosis was established in all cases preoperatively by curettage of endometrium. Many patients were treated by radical hysterectomy with pelvic lymph node dissections. However, in 21 patients, lymph node dissection was not performed because of their age and complications. All patients were staged according to the Federation of International Gynecology and Obstetrics (FIGO) classification, and their tumors were graded as well differentiated (G1, $\leq 5\%$ solid components), moderately differentiated (G2, 6-50% solid components), or poorly differentiated (G3, $\geq 50\%$ solid components). In this study, the investigation was limited to endometrioid adenocarcinoma because of the small number of other histological types. Adjuvant chemotherapy was administered to stage I patients with risk factors such as high histological grade and the like, and to all stage II, III, and IV patients. Two to three weeks after surgery, these patients were subjected to 4-6 cycles of cisplatin-based chemotherapy. Median follow-up time of surviving patients was 55.3 months, ranging from 20 to 120 months. All subjects were examined every 3 months for the first 2 years and every 6 months thereafter.

The status of each stage is as follows.

Stage I: carcinoma tissue is present only in the endometrium

Stage II: carcinoma spreads to the uterine cervix beyond the endometrium

Stage III: carcinoma spreads outside of the uterus, but not outside of the small pelvis Stage IV: carcinoma spreads beyond the small pelvis to other parts of the body, or reaches to the bladder or rectum (2) P-LAP Immunostaining Informed consent was obtained from each patient for sample use. All tissue samples were fixed in 10% formalin, embedded in paraffin, and routinely stained with hematoxylin and eosin for histological examination.

Anti-human P-LAP polyclonal antibody was prepared according to the method disclosed in PLACENTA, 2000, vol.21, p. 628-634. Immunohistochemical staining was performed using the avidin-biotin immunoperoxidase technique (Histofine SAB-PO kit, Nichirei, Tokyo, Japan). Sections were cut at a thickness of 4 µm, and immunostained by streptavidin-biotin-peroxidase method. Areas containing viable carcinoma cells were confirmed by pathologists and selected. Deparaffinized sections in 0.01 M citrate buffer were treated three times for 5 minutes at 90° C. at 750 W with an H2500 microwave oven. Sections were incubated with 0.3% hydrogen peroxide for 20 minutes and then further incubated with 10% normal goat serum. Anti-human P-LAP polyclonal antibody (0.4 µg/section) was added to the tissue sections and incubated for 1 hour. The binding of the antibodies was followed with biotinylated goat anti-rabbit IgG and horseradish peroxidase-conjugated streptavidin (Histofine SAB-PO, Nichirei, Tokyo, Japan). Chromogenic development was performed by immersion of the sections in 3-amino-9-ethylcarbazole (AEC, Nichirei, Tokyo, Japan). The slides were counterstained with Mayer's hematoxylin. To assess the specificity of the reaction, there was a negative control in all cases. The negative control slide was prepared from the same tissue block. Immunostaining intensity was scored semi-quantitatively on a three-tiered scale (negative =−, weakly positive=+, strongly positive=++) relative to the known positive and negative controls. Both routine hematoxylin and eosin slides and P-LAP reaction were reviewed independently by two pathologists.

(3) Statistical Analysis

The association between distribution of P-LAP and clinicopathologic characteristics were evaluated using the Fisher exact test or Chi-square test. The Kaplan-Meier method was used to summarize the distributions of disease-free interval. Log-rank test was used to evaluate individual factors with respect to these outcomes and the step-wise Cox proportional hazards model was used to assess multiple factors simultaneously. Patients who died without evidence of disease recurrence were censored as of the date of death. For comparison between two parameters, p less than 0.05 were considered significant.

(4) Results

The protein expression and cellular localization of P-LAP were analyzed by immunohistochemical staining of the tissue sections obtained from human endometrial endometrioid adenocarcinoma patients.

FIG. 1A shows the representative of P-LAP staining exhibited weakly positive in G1 endometrioid adenocarcinoma. FIG. 1B shows the representative of strongly positive in G1 endometrioid adenocarcinoma. The strongest immunoreactivity for P-LAP was focused in the area with tumor cell invasion to the myometrial layer of G2 and G3 endometrioid adenocarcinoma (FIG. 1C, D). Normal endometrial cells were either negative or weakly positive.

The median age of the patients was 58.5 years (range, 36-75). Of 99 cases, 69 cases (69.7%) had specific P-LAP immunostaining. Weak staining was detected in 38 cases (38.4%) and strong staining in 31 cases (31.3%). Table 1 shows the relationships between P-LAP and some clinical characteristics, including histological grade, surgical stage of disease, myometrial invasion, lymph node involvement and vascular infiltration, etc.

TABLE 1

| Characteristics | Total number of patient (%) | Number of patient showing strongly positive for P-LAP (%) | P |
|---|---|---|---|
| Age | | | |
| <60 | 61 (61.6) | 21 (34.4) | 0.51 |
| ≧60 | 38 (38.4) | 10 (26.3) | |
| Surgical Stage | | | |
| I–II | 77 (77.8) | 20 (26.0) | 0.02[a] |
| III–IV | 22 (22.2) | 11 (50.0) | |
| Grade (differentiation stage) | | | |
| 1 | 55 (55.6) | 4 (7.2) | <0.01[b] |
| 2 | 29 (29.3) | 18 (62) | |
| 3 | 15 (15.1) | 9 (60) | |
| Myometrial invasion | | | |
| none | 11 (11.1) | 0 (0) | 0.01[b] |
| ½ or less | 53 (53.5) | 11 (20.8) | |
| ½ or more | 35 (35.4) | 20 (57.1) | |
| Vascular infiltration | | | |
| negative | 29 (29.3) | 16 (55.2) | <0.01[a] |
| positive | 70 (70.7) | 15 (21.4) | |
| Lymph node involvement | | | |
| negative | 10 (10.1) | 7 (70) | <0.01[b] |
| positive | 68 (68.7) | 18 (26.4) | |

[a]Fisher exact test
[b]Chi-square test

The present inventors found no significant correlation between P-LAP and, patient age. P-LAP was established as strongly positive in 7.2% of G1 cases, in 62% of G2 cases, and in 60% of G3 cases. The present inventors found a positive correlation between P-LAP and histological grade (p<0.01). The present inventors also found a positive correlation between P-LAP and surgical stage of disease (p=0.02), muscular invasion (p=0.01), lymph node involvement (p<0.01), and vascular infiltration (p<0.01).

Figure 2:
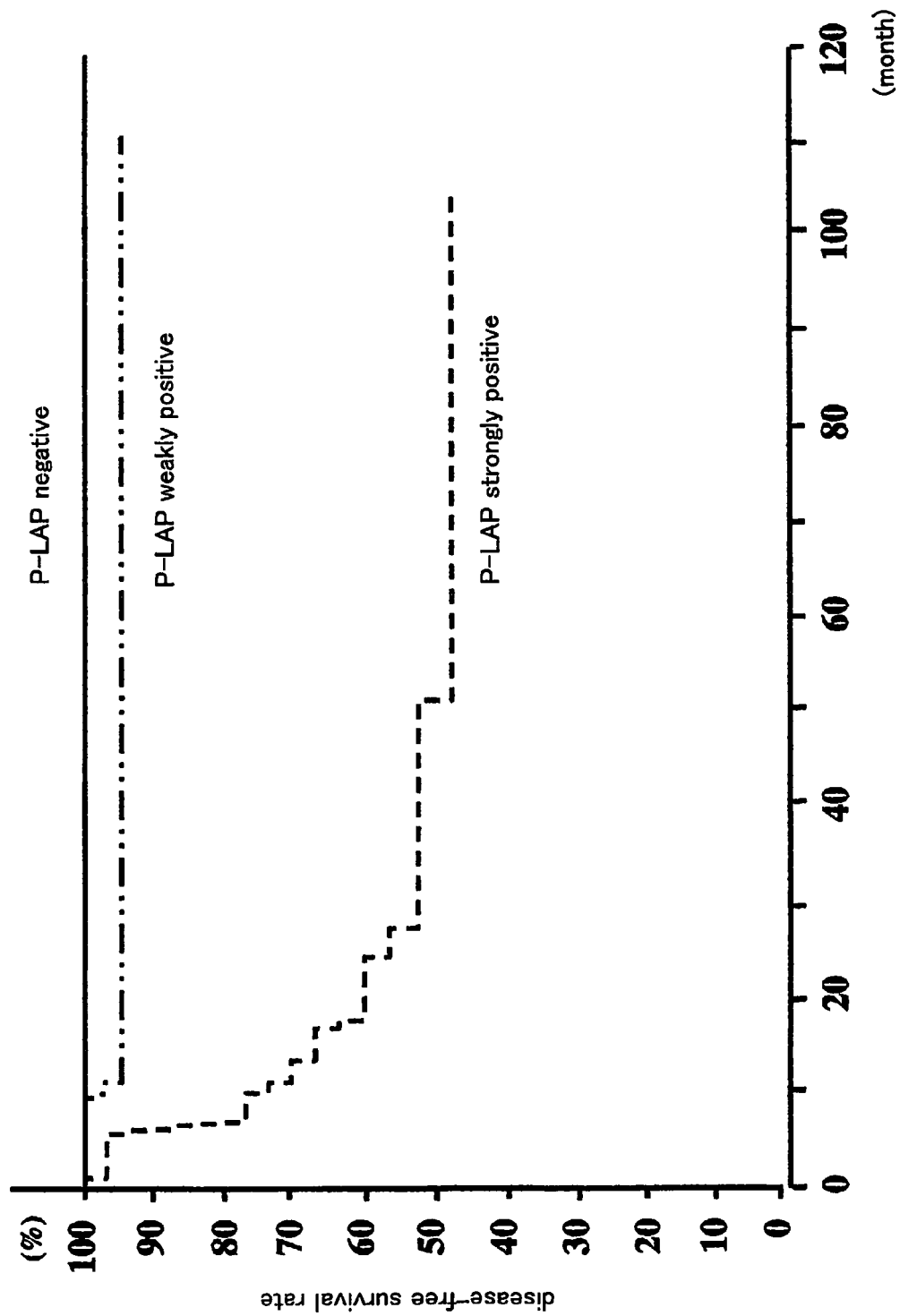
FIG. 2 shows correlation between P-LAP immunoreactivity and disease-free interval in endometrial endometrioid adenocarcinoma patients.
Figure 3:
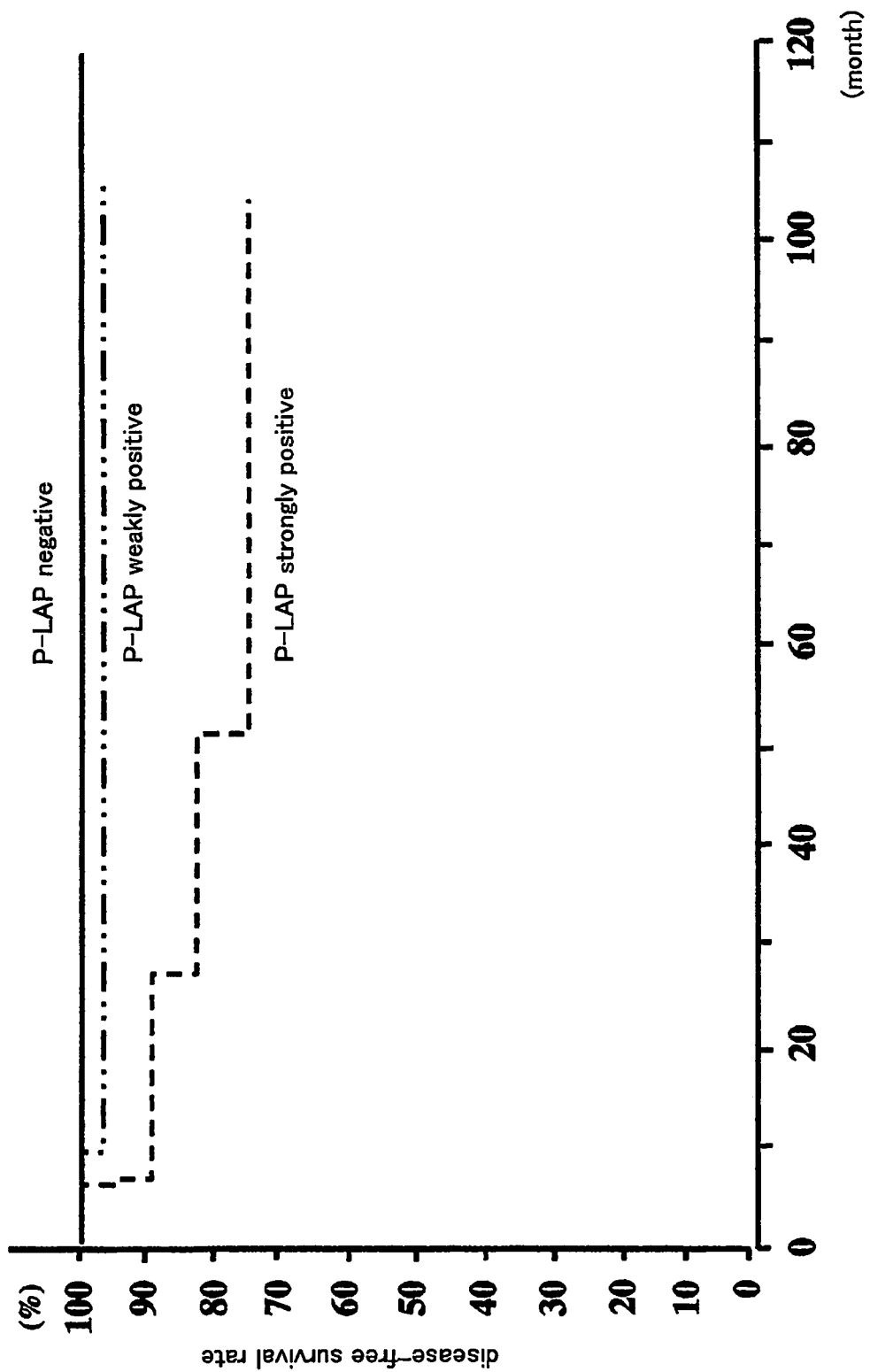
FIG. 3 shows correlation between P-LAP immunoreactivity and disease-free interval in early stage endometrial endometrioid adenocarcinoma patients.
Figure 4:
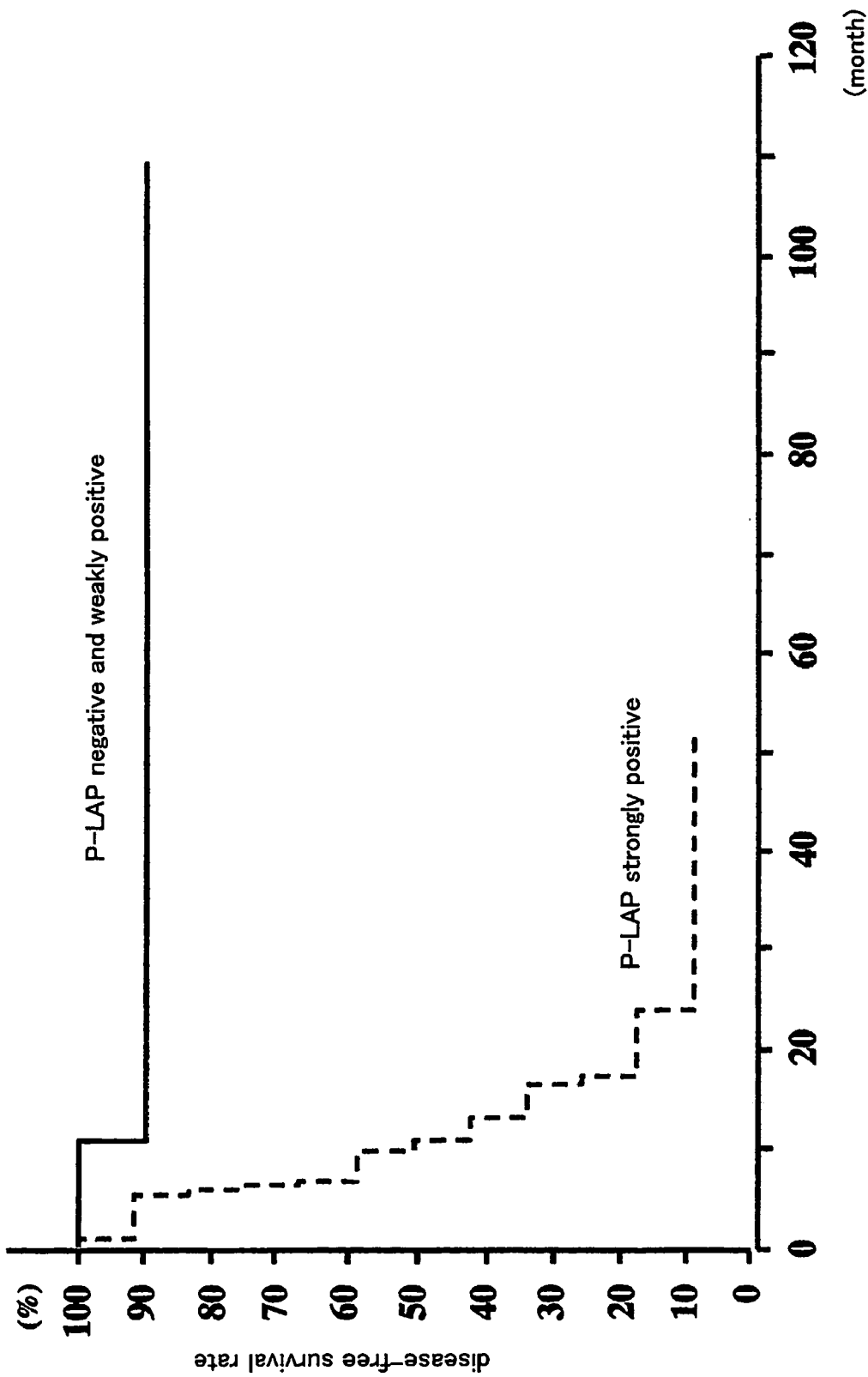
FIG. 4 shows correlation between P-LAP immunoreactivity and disease-free interval in advanced stage endometrial endometrioid adenocarcinoma patients.

Disease-free interval curves were drawn by Kaplan-Meier method to evaluate the prognostic impact of P-LAP expression. The 10-year disease-free survival rates (DFS) of patients who had negative, weakly positive, and strongly positive expressions for P-LAP were 100%, 94.7%, and 47.3%, respectively (FIG. 2). Patients with strongly positive P-LAP staining showed a significantly lower disease-free interval compared with patients showing negative or weakly positive P-LAP staining (p<0.01). Furthermore, the analysis of disease-free interval was performed separately in early stage (stage I-II; n=77) and advanced stage (stage III-IV; n=22) patients. In the early stage patients, the 10-year disease-free survival rate among those showing negative, weakly positive, and strongly positive expression for P-LAP were 100%, 96.6%, and 73.9%, respectively (FIG. 3). Patients with strongly positive P-LAP staining also showed a significantly lower disease-free interval compared with that of patients showing negative or weakly positive P-LAP expression (p<0.05). In the advanced stage, only one patient was negative for P-LAP, so this patient was included among patients with weakly positive P-LAP expression. The 10-year disease-free survival rates of patients who had negative or weakly positive expression for P-LAP was 90%, and was 8.3% for those who had strongly positive expression with the difference being significant (p<0.01) (FIG. 4).

Table 2 shows the univariate and multivariate analysis of disease-free interval according to the clinical characteristics and P-LAP status.

TABLE 2

| Parameter | Category | Univariate analysis P | Multivariate analysis | | |
|---|---|---|---|---|---|
| | | | odds ratio | 95% CI | P |
| Age | <60 ≧60 | 0.07 | 1.02 | 0.95-1.08 | 0.55 |
| Surgical stage | I/II III/IV | <0.01 | 8.78 | 2.77-27.8 | <0.01 |
| P-LAP | Negative/Weakly positive Strongly positive | <0.01 | 12.8 | 2.84-58.8 | <0.01 |
| Grade (differentiation stage) | ½ 3 | 0.02 | — | — | — |
| Myometrial invasion | negatiave or ½ or less ½ or more | 0.14 | — | — | — |
| Vascular infiltration | Positive Negative | 0.06 | — | — | — |

95% CI: 95% confidence interval

Lymph node metastasis was excluded as a factor in these analyses since 21 patients did not undergo lymphadenectomy. Univariate analysis demonstrated that the following factors were significant: surgical stage, tumor grade (differentiation stage), and P-LAP expression. These factors were further analyzed by multivariate methods. Multivariate analysis demonstrated that P-LAP expression and surgical stage were independent prognostic factors.

Example 2

The prognostic impact of P-LAP expression on patients with ovarian carcinoma who had been surgically treated was evaluated according to the same method as described in Example 1.

Of 61 patients (median age: 52.5, age range: 33-78), the numbers of patients showing negative, weakly positive, and strongly positive expression for P-LAP are 12, 20, and 29, respectively.

The 10-year disease-free survival rates of patients who had negative expressions for P-LAP and patients who had weakly positive expressions for P-LAP were both 75%, while the 10-year disease-free survival rate of patients who had strongly positive expressions for P-LAP was 48.3%. As mentioned above, patients showing strongly positive P-LAP staining showed a significantly lower disease-free survival rate compared with that of patients showing negative or weakly positive P-LAP staining (p<0.05).

INDUSTRIAL APPLICABILITY

The reagent and the method for determination of the present invention can be used for prognostic evaluation of carcinoma, thus they are useful in the field of pharmaceuticals and medical treatment.

The invention claimed is:
1. A method for prognostic evaluation of a P-LAP positive ovarian carcinoma in a patient, comprising:

(a) contacting P-LAP positive ovarian carcinoma tissues obtained from said patient with an anti-P-LAP antibody,
(b) measuring the intensity of the specific antigen-antibody binding between P-LAP present in the ovarian carcinoma tissues and anti-P-LAP antibody, and
(c) correlating the intensity of the specific antigen-antibody binding with a ten year disease free survival rate (DFS) of said patient.

2. The method as claimed in claim 1, wherein the anti-P-LAP antibody is an anti-human P-LAP antibody.

3. The method as claimed in claim 1, wherein the anti-P-LAP antibody is an anti-human P-LAP polyclonal antibody.

* * * * *